Figure 1:
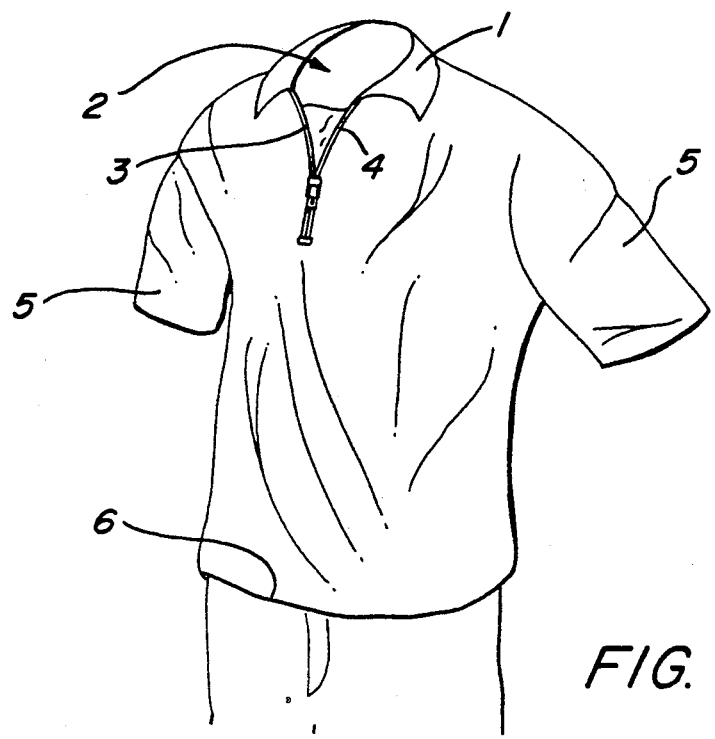

United States Patent [19]

Dordevic

[11] Patent Number: 5,103,504
[45] Date of Patent: Apr. 14, 1992

[54] TEXTILE FABRIC SHIELDING ELECTROMAGNETIC RADIATION, AND CLOTHING MADE THEREOF

[75] Inventor: Zoran Dordevic, Beograd, Yugoslavia

[73] Assignee: Finex Handels-GmbH, Munich, Fed. Rep. of Germany

[21] Appl. No.: 494,758

[22] Filed: Mar. 16, 1990

Related U.S. Application Data

[63] Continuation-in-part of Ser. No. 394,001, Aug. 15, 1989, abandoned.

[30] Foreign Application Priority Data

Feb. 15, 1989 [YU] Yugoslavia ............... 336/89
Jun. 22, 1989 [DE] Fed. Rep. of Germany ....... 8907655

[51] Int. Cl.$^5$ ............................................. G21F 3/02
[52] U.S. Cl. ............................................. 2/243 A; 2/2; 2/69; 139/425 R; 250/516.1
[58] Field of Search ............ 57/901; 174/35 R; 2/2.5, 69, 243 A, DIG. 7, 2; 139/425 R, 425 A; 250/515.1, 516.1; 428/224, 225, 227, 242, 340

[56] References Cited

U.S. PATENT DOCUMENTS

| | | | |
|---|---|---|---|
| 3,288,175 | 11/1966 | Valko | 139/425 |
| 3,310,053 | 3/1967 | Greenwood | 250/516.1 X |
| 3,699,590 | 10/1972 | Webber et al. | 57/901 X |
| 3,882,667 | 5/1975 | Barry | 57/901 X |
| 3,986,530 | 10/1976 | Maekawa | 57/901 X |
| 3,987,613 | 10/1976 | Woods et al. | 428/359 |
| 4,196,355 | 4/1989 | Maine | 250/516 |
| 4,220,867 | 9/1980 | Bloch, Jr. | 250/516.1 |
| 4,435,465 | 3/1984 | Ebneth et al. | 428/242 |
| 4,466,135 | 8/1984 | Coppage, Jr. | 2/2.5 |
| 4,533,591 | 8/1985 | Sorko-Ram | 428/242 |
| 4,590,623 | 5/1986 | Kitchman | 2/69 X |
| 4,643,938 | 2/1987 | Oyama et al. | 428/268 |
| 4,653,473 | 3/1987 | Kempe | 139/425 R X |
| 4,766,608 | 8/1988 | Cusick et al. | 2/DIG. 7 |
| 4,793,130 | 12/1988 | Togashi et al. | 57/901 X |
| 4,810,575 | 3/1989 | Guevel et al. | 428/242 |
| 4,889,963 | 12/1989 | Onai | 428/242 |

FOREIGN PATENT DOCUMENTS

| | | | |
|---|---|---|---|
| 2642854 | 4/1977 | Fed. Rep. of Germany | 250/516.1 |
| 2923286 | 12/1979 | Fed. Rep. of Germany | |
| 88041.7 | 11/1988 | Fed. Rep. of Germany | |
| 2311117 | 12/1976 | France | |
| 1118667 | 5/1989 | Japan | 428/242 |
| 1474300 | 5/1977 | United Kingdom | |

*Primary Examiner*—Werner H. Schroeder
*Assistant Examiner*—Amy Brooke Vanatta
*Attorney, Agent, or Firm*—Price, Gess & Ubell

[57] ABSTRACT

Textile fabric shielding electromagnetic radiation, and clothing made thereof. The textile fabric is made of threads spun of textile fibers, containing cotton, and of steel fibers having a diameter of 6 to 10 μm. The number of mixed yarn threads in warp direction and in weft direction each is 18 to 20 threads per cm, and the yarn fineness of the textile fabric is especially 38 to 40 tex. The textile fabric guarantees a shielding of 20 to 40 dB against electromagnetic radiation at a frequency of 10 GHz. The fabric has the quality of usual clothing, and the clothing thereof is designed with respect to proportions, seams, fasteners, and other special features in a manner such that especially people wearing pacemakers, or hospital and radar personnel, are protected against electromagnetic radiation.

14 Claims, 3 Drawing Sheets

TEXTILE FABRIC SHIELDING ELECTROMAGNETIC RADIATION, AND CLOTHING MADE THEREOF

The invention concerns a textile fabric shielding electromagnetic radiation, and clothing made thereof. This application is a continuation-in-part of United States patent application Ser. No. 394,001, filed Aug. 15, 1989, now abandoned.

From DE-A-29 23 286, a textile fabric is known whose orthogonally crossing warp threads and weft threads are made of spun mixed yarn of steel fibres of stainless steel and of textile fibres. The steel fibres may be extremely thin, less than 25 micrometers in diameter, for example. According to this document, the mesh is proposed to measure at least 0.5 cm. This textile fabric is designed for carpet floors or working garments, for example, in order to obtain an antistatic network and thus prevent electrostatic charging.

However, such a fabric does not provide effective protection against microwaves and other electromagnetic radiation, to which in particular the hospital personnel, for example, when operating electromedical equipment such as X-ray, ECG and EEG apparatus and the like, and the personnel for operating radar installations, for example, are exposed. In the course of electronization, also heart pacemakers are miniaturized and refined, but at the same time rendered susceptible to electromagnetic radiation interference such as occurs in everyday life due to, for example, broadcast and TV stations and various electrical apparatus, electric motors, electrical and electronic ignition control devices in motor vehicles, shavers, electrical household appliances, and electronic computer installations and the like. Modern heart pacemakers are designed so as to take over the pacemaker function only when the normal heart rhythm is disturbed, but not to interfere when the heart rhythm is normal. The occurrence of electromagnetic radiation, however, may result in a disturbance of the heart pacemaker control such that incorrect information on the current heart activity may be received and the control may fail in that case.

While it is true that clothing which shields against electromagnetic radiation exist, such as the vest known from US-A-4 196 355. However, this vest, due to its construction and weight, is much too heavy and uncomfortable to be suitable for normal applications.

According to the invention, a textile fabric and clothing made thereof are provided, which are effectively suitable for shielding against electromagnetic radiation, in particular in the microwave range, and, at the same time, do not restrict the wearing comfort of usual clothing.

The invention is based on the perception that total shielding against electromagnetic radiation is not necessary, since radiation below certain intensities can be accepted without health impairment, and that this provides the possibility of achieving sufficient shielding by means of clothing even without restriction on the wearing comfort.

For shielding against electromagnetic radiation, the invention provides a textile fabric whose orthogonally crossing warp threads and weft threads are made of spun mixed yarn of steel fibers of stainless steel and of textile fibers. To this end, the textile fabric has the quality of fabrics for usual clothing, wherein the textile fibers comprise cotton fibers and are twined with the steel fibers which measure 6 to 10 micrometers in diameter and constitute a content of 10 to 15% per weight of the mixed yarn, the distribution of the warp threads and the weft threads in the fabric and the composition of the warp threads and the weft threads being substantially the same, the number of mixed yarn threads in warp direction and in weft direction each is 18 to 20 threads per cm, and the yarn fineness of the textile fabric is in the range of 30 to 50 tex (g per km), especially of 38 to 40 tex, such that a shielding by 20 to 40 dB against electromagnetic radiation at a frequency of 10 GHz is established by the fabric.

Owing to the content and fineness of steel fibers suggested in accordance with the invention, a textile fabric suitable for effective shielding against excessive electromagnetic microwave radiation can be obtained in a clothing fabric quality, which textile fabric is not too stiff. Hence, clothing can be made which is comparable to clothing without steel fibers. For the shielding effect, it is essential that the steel fibers and the textile fibers are spun and twined with each other in a manner such that a substantial part of the steel fibers is exposed on the exterior surface of the mixed yarn and sufficient mutual electrical contact of the fibers is achieved in the warp and weft threads at the crossings of the fabric to form a Faraday cage. The average number of the steelfibers in the yarn cross-section is preferably 10 to 15.

Preferably, the thickness of the steel fibers measures 8 micrometers, and the content of the steel fibers in the mixed yarn is preferably 13.5% per weight. The length of the steel fibers is preferably in the range of the length of the cotton fibers and, hence, measures 3 to 10 centimeters. Although it is further possible to provide a mixture of cotton fibers and polyamide fibers, it is preferred to provide textile fibers exclusively of cotton. Cotton is capable of absorbing moisture and improves the electrical conductibility with increasing moisture absorption.

Although a twined one-thread yarn, i.e., a yarn only single-twined, may be used, it is preferred to use a mixed yarn made of double-twined mixed yarn threads, each of which is made of textile fibers and steel fibers in a twined manner, wherein the single threads have a yarn fineness of 16 to 20 tex and a degree of turns of 550 to 650 turns, especially Z-turns, per m, and wherein the degree of turns of the double-threads is 400 to 480 turns, especially Z-turns, per m.

The textile fabric according to the invention is light (the weight of the textile fabric is preferable in the region of 160 g per m$^2$) and permeable to air and washable like other cloths without impairment of the shielding effect against electromagnetic radiation as would be the case if there were no discrete steel fibers but, instead, for example, a metal coating of the textile fibers. Moreover, the textile fabric according to the invention may be dyed such that pleasing and fashionable articles of clothing can be made of it.

A textile fabric according to the invention having been proved and being excellently effective to shield heart pacemaker against microwave radiation was made of pure cotton with spun with steel fibers. The warp threads and weft threads were made of double-twined yarn of a fineness of R 38 to 40 tex made of single-threads of a fineness of R 16 to 18 tex. The degree of turns of the single threads was 590 to 640 Z per m and that of the Yarn was 420 to 440 Z per m. The content of steel fibers spun into the single-threads was about 13.5% per weight of the mixed yarn. The thread density of the textile fabric was 18 to 20 threads per cm, each, in warp direction and in weft direction and the average weight of the textile fabric was 160 g per m². The textile fabric had an elongation of 9 to 14% at a breaking force of 638 to 672 N.

The clothing according to the invention is completely or partly made of a textile fabric according to the invention. This textile fabric may completely form the clothing or may be provided as its interior lining. It is also possible to line the textile fabric itself with a lining of different textile material. For the manufacture of this textile fabric, usual pieces of fabric are cut out which are sewed together along joint seams. According to the invention, it is essential that the textile fabric is made of the above-presented textile/steel-fiber fabric according to the invention and covers at least the upper part of the body and the hip area of the person wearing the clothing as well as at least the person's upper arms approximately to the elbows. To avoid interruption of the shielding effect in the area of the joint seams, the joint seams should be turned up into each other and sewed together by at least two seams with a sewing yarn that is also a textile-fiber/steel-fiber mixed yarn of the kind according to the invention. However, the content of steel fibers in the sewing yarn may possibly be greater than the content in the threads of the textile fabric. All fasteners of the clothing, such as zip and button fasteners, should be free of metal and be underlayed with an interior border band or flap made of the textile-fiber/steel-fiber fabric according to the invention and provide an overlap breadth of at least 5 and preferably 7 centimeters. If pockets are provided in the textile fabric, these pockets should not be inserted into but put on the fabric, in order to avoid interruptions of the shielding effect.

In a preferred embodiment of a clothing according to the invention, the clothing is in the form of a shirt or T-shirt which has at least elbow-length sleeves, covers the hip area of the person wearing the shirt and is provided with a closable neckline that, even when not closed, is covered by an interior flap made of the textile-fiber/steel-fiber fabric according to the invention. As proven by numerous experiments, such a clothing is most suitable for wearers of heart pacemakers to attain an effective shielding of the heart pacemaker against electromagnetic radiation disturbances and, at the same time, achieving the wearing comfort of other shirts or T-shirts. Owing to the invention, shirts or T-shirts of this kind may be manufactured in such a way that they look like other shirts or T-shirts and, hence, the fact that a person needs a heart pacemaker is not discernible from this kind of clothing.

In another preferred embodiment, clothing according to the invention suitable for the personnel of radar installations takes the shape of an overall, in which the textile-fiber/steel-fiber fabric according to the invention covers the upper part of the body as well as at least the upper arms and the hip area, at least down to the knees.

As protective clothing for hospital staff against the influence of electromagnetic radiation emitted by electromedical apparatus, two-piece clothing consisting of a jacket or blouse and a pair of trousers is suggested, wherein the pair of trousers is overlapped by the jacket or blouse by at least 10 centimeters and the jacket or blouse in its chest area has overlapping parts of textile-fiber/steel-fiber fabric held together by Velcro-type fasteners. Since clothing according to the invention is made of comfortable textile material, it can be worn completely closed, while the Velcro-type fasteners prevent the jacket or blouse from being worn open. In this arrangement, one of the overlapping parts of textile fabric preferably extends to ne shoulder of the wearing person, and the other part of textile fabric extends at least to the middle of the person's body. The waist measurement of the trousers of this clothing is preferably also adjustable by means of Velcro-type fasteners. In such clothing according to the invention, an interior lining may be formed of the textile-fiber/steel-fiber fabric according to the invention, while the exterior side of the clothing may, for example, made of light cotton cloth of a quality usual for hospital clothing.

When the clothing according to the invention is embodied by an overall or two-piece suit, a stand-up collar containing textile fabric material according to the invention is preferably additionally provided.

Figure 2:
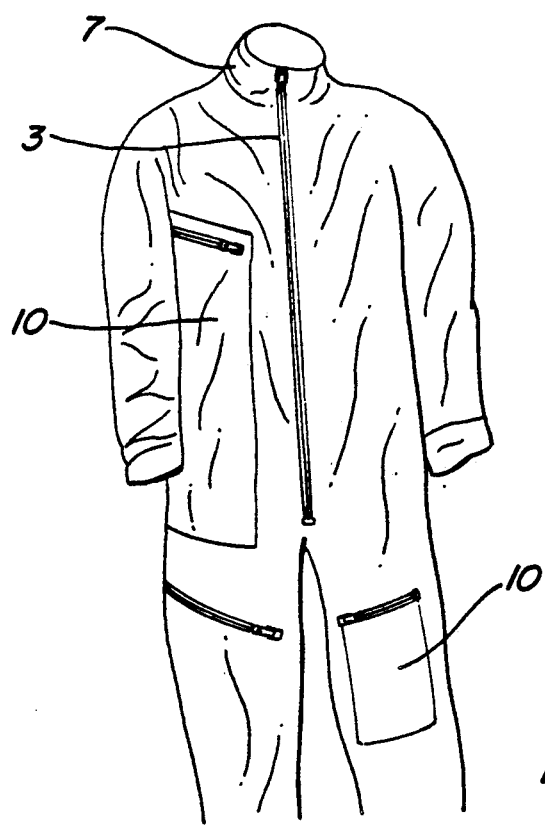
Figure 3:
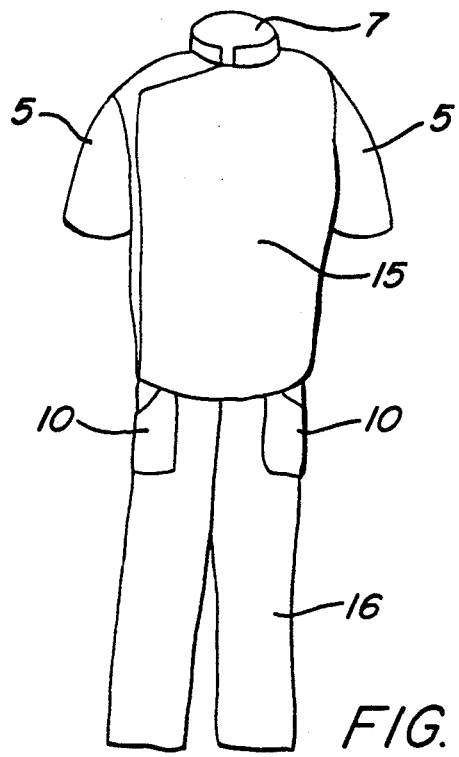
Figure 4:
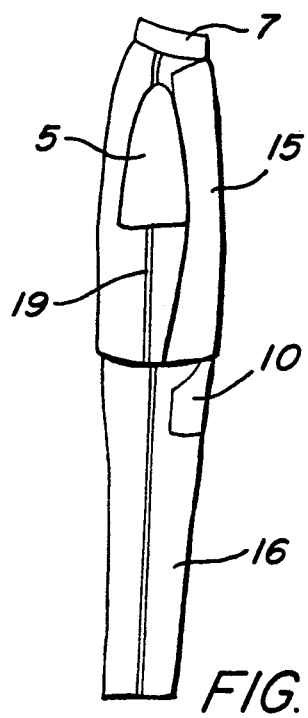
Figure 5:
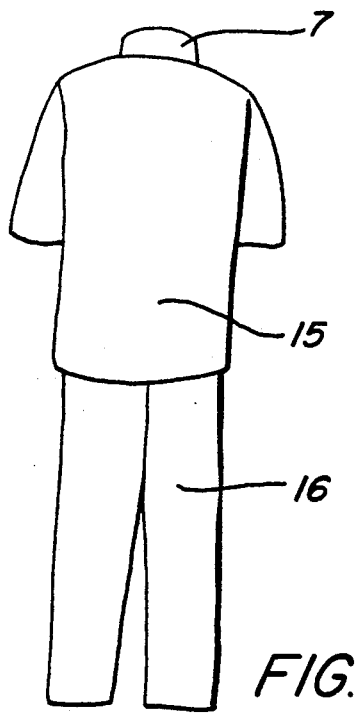
Figure 10:
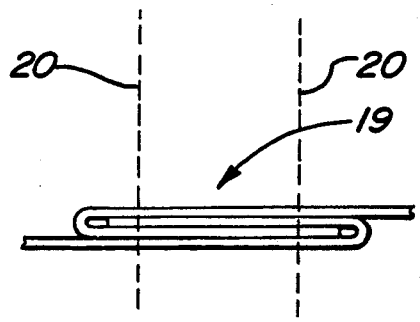
Figure 6:
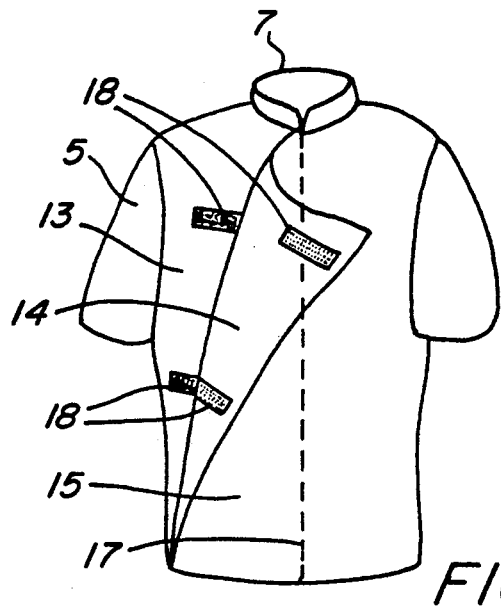
Figure 7:
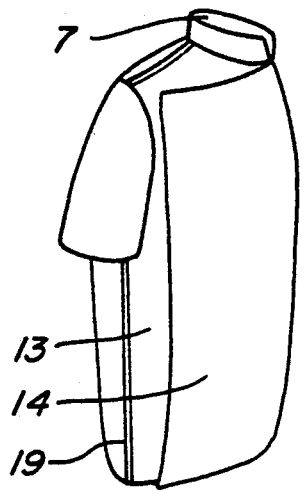
Figure 8:
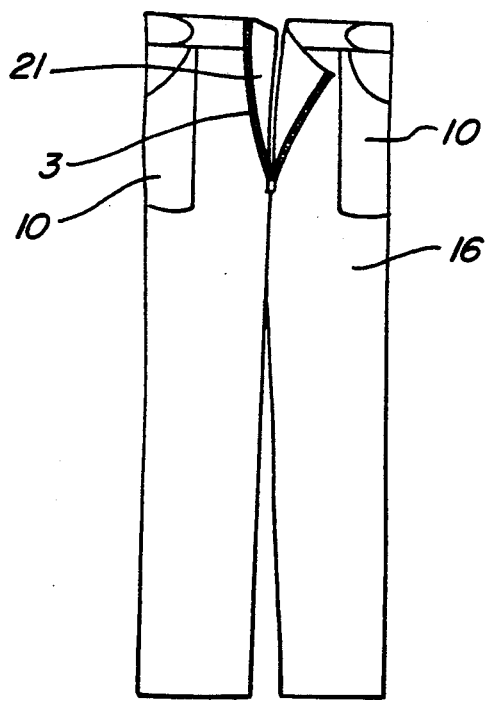
Figure 9:
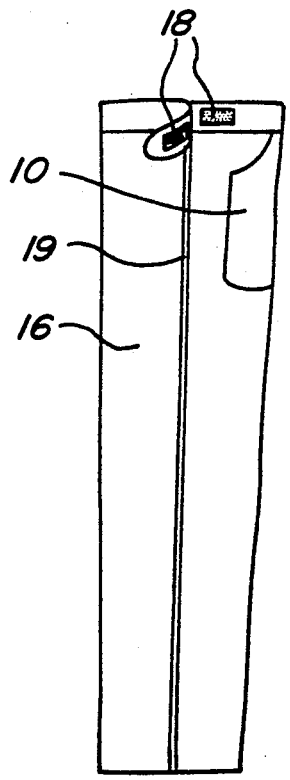

The invention will now be explained with regard to clothing according to the invention and depicted in the drawings. In the drawing:

FIG. 1 illustrates clothing according to the invention in the form of a T-shirt or shirt, FIG. 2 illustrates clothing according to the invention in the form of an overall, FIGS. 3 to 5 illustrates clothing according to the invention in the form of a two-piece suit from the front, lateral and rear sides, FIGS. 6 and 7 illustrate front and side views of the jacket of the clothing according to FIGS. 3 to 5, FIGS. 8 and 9 illustrate front and side views of pair of trousers of the clothing according to FIGS. 3 to 5, and FIG. 10 illustrates the design of the joint seams of the clothing according to FIGS. 3 to 9.

The T-shirt or shirt according to FIG. 1 is provided for persons wearing a heart pacemaker and is designed to shield the heart pacemaker against electromagnetic radiation, especially in the microwave range. For this purpose, the T-shirt is made of the fabric described in detail above which is woven from a mixed yarn of cotton and steel fibers intertwined with each other. The T-shirt completely covers the upper part of the body of the wearer, and clearly extends with its lower rim 6 beyond the hip area of the wearer. The neckline 2 of the T-shirt equipped with a folded collar 1 can be closed by means of a zip fastener 3 of plastic material, the zip fastener being underlayed with an interior flap 4 completely covering the neckline 2 even when the zip fastener 3 is completely open. The interior flap 4 is made of the same textile fabric material as the other parts of the T-shirt, whose sleeves 5 are elbow-length so that no detrimental radiation can intrude laterally from the sleeves 5, either. These sleeves 5 should be at least 20 centimeters long.

The overall according to FIG. 2 may, for example, be used as working clothing for radar personnel and is also made of the textile fabric parts according to the invention. The overall can be closed up to the upper rim of the stand-up collar 7 by means of the zip fastener 3, is also made of plastic material, and is underlayed over its entire length with an interior border band (not shown) which is at least 7 centimeters broad and made of the textile fabric material. The pockets 10 are put on the textile fabric material and sewed to it. These pockets may be made of a different textile cloth.

The two-piece protective suit according to FIGS. 3 to 9 is provided as protective clothing for hospital personnel exposed to microwave radiation arising from electromedical apparatus. The jacket, as well as the trousers of this protective suit, are made of an outer cloth such as light cotton fabric material developing no protective effect, and of a lining made of the textile fabric material according to the invention. This lining extends over the entire clothing. The front part of the jacket has a widened outer portion 14 extending up to one shoulder and an inner portion 13 extending with its interior border 17 to the middle of the chest. The jacket is closed by means of Velcro-type fastener strips 18 when laying together the outer portion 14 on the inner portion 13. The jacket 15 is provided with a stand-up collar 7 and elbow-length sleeves 5.

The pair of trousers 16 can be closed in the front by means of a zip fastener 3 which is underlayed with a particularly wide interior border band 21 of a width of at least 5 centimeters. The waist measurement of the trousers is adjustable by means of Velcro-type fastener strips 18. In addition, the trousers have put-on pockets 10.

The respective clothing according to FIGS. 1 to 9 are tailored of fabric pieces which are sewed together along joint seams 19. As can be seen from FIG. 10, the joint seams 19 are turned up into each other and sewed together by at least two seams 20.

I claim:

1. A textile clothing fabric comprising orthogonal crossings between warp threads and weft threads, the threads being made of stainless steel fibers and textile fibers blended together and spun into mixed yarn, wherein the textile fibers comprise cotton fibers and are twined with the steel fibers, the steel fibers measure 6 to 10 micrometers in diameter and constitute a content of 10 to 15% per weight of the mixed yarn, the distribution of the warp threads and the weft threads in the fabric and the composition of the warp threads and the weft threads being substantially the same, the number of mixed yarn threads in warp direction and in weft direction each is 18 to 20 threads per cm, the yarn fineness of the textile fabric is in the range of 30 to 50 tex, a part of the steel fibers is exposed on the exterior surface of the mixed yarn and mutual electrical contact exists between the warp and weft threads at said crossings to form a Faraday cage, such that a shielding by 20 to 40 dB against electromagnetic radiation at a frequency of 10 GHz is established by the fabric.

2. The textile fabric of claim 1, wherein the mixed yarn is made of double-twined mixed yarn threads comprised of two twined single threads, each of which is made of textile fibers and steel fibers in a twined manner, wherein the single threads have a yarn fineness of 16 to 20 tex and a degree of turns of 550 to 650 turns per m, and wherein the degree of turns of the double-threads is 400 to 480 turns per m.

3. The textile fabric of claim 1, wherein the fiber thickness of the steel fibers measured 8 micrometers, and the content of the steel fibers in the mixed yarn is 13.5% per weight of the mixed yarn.

4. The textile fabric of claim 1, wherein the length of the steel fibers is 3 to 10 micrometers.

5. The textile fabric of claim 1, wherein the textile fibers are made only of cotton.

6. The textile fabric of claim 1, wherein the weight of the textile fabric is 130 to 190 g per $m^2$.

7. Clothing for a human wearer, the clothing being completely or partly made of one piece of textile clothing fabric, the clothing being constructed to cover at least an upper part of the body and a hip area of the wearer, and further comprising a neck-chest area and sleeves, the piece of textile fabric comprising fabric parts sewed together along joint seams and being adapted to be opened and closed by means of a fastener at least in the neck-chest area, characterized in that the textile clothing fabric has the features of any of claim 1 to 6, the sleeves being at least elbow-length, the joint seams being turned up into each other and sewed together by at least two seams of sewing yarn composed of the mixed yarn, the fastener being free of metal and being underlaid with an interior border band or flap of the textile clothing fabric having a breadth of at least 5 centimeters.

8. The clothing of claim 7, wherein the textile fabric is provided with pickets made of a cloth sewed onto said textile clothing fabric.

9. The clothing of claim 7, wherein the clothing further comprises a T-shirt having elbow-length sleeves and is made of steel fibers and textile fibers.

10. The clothing of claim 7, wherein the clothing further comprises a one-piece overall having a stand-up collar and wherein the textile fabric covers the legs of the wearer at least down to the knees.

11. The clothing of claim 7, wherein the clothing is comprised of a jacket and trousers, and wherein the trousers are overlapped by the jacket by at least 10 centimeters, and the jacket or blouse, has at least first and second textile fabric parts overlapping each other and being held together by fasteners connecting the textile fabric parts with each other.

12. The clothing of claim 11, wherein the first overlapping textile fabric part extends to one shoulder of the wearer, and the second textile fabric part extends at least to the middle of the body when the jacket is closed.

13. The clothing of claim 11, wherein adjustability of a waist portion of the trousers is provided by means of fasteners made of plastic material.

14. The clothing of claim 11, wherein the jacket has a stand-up collar made of the fabric of steel fibers and textile fibers.

* * * * *